United States Patent [19]

Tsuda

[11] Patent Number: 4,569,911

[45] Date of Patent: Feb. 11, 1986

[54] METHOD OF MAKING ASPARTIC ACID AND PURIFYING ASPARTASE

[75] Inventor: Yoshihisa Tsuda, Wilmette, Ill.

[73] Assignee: UOP Inc., Des Plaines, Ill.

[21] Appl. No.: 572,107

[22] Filed: Jan. 19, 1984

[51] Int. Cl.$^4$ .................. C12P 13/20; C12N 9/96; C12N 9/88; C12R 1/125

[52] U.S. Cl. .................. 435/109; 435/188; 435/232; 435/814; 435/839

[58] Field of Search ........... 435/188, 109, 232, 814

[56] References Cited

U.S. PATENT DOCUMENTS

| | | | |
|---|---|---|---|
| 3,214,345 | 10/1965 | Chibata et al. | 195/30 |
| 3,791,926 | 2/1974 | Chibata et al. | 195/30 |
| 4,141,857 | 2/1979 | Levy et al. | 435/180 X |
| 4,391,910 | 7/1983 | Kimura et al. | 435/232 |

OTHER PUBLICATIONS

Agricultural and Biological Chemistry, vol. 29, No. 7, pp. 665–671, (1965).

*Primary Examiner*—Lionel M. Shapiro
*Attorney, Agent, or Firm*—Thomas K. McBride; William H. Page, II; Eugene I. Snyder

[57] ABSTRACT

The aspartase from a mutant *Bacillus subtilis*, NRRL B-15536, is produced in relatively high cell yield within a comparatively short time. The enzyme converts fumaric acid to L-aspartic acid stoichiometrically with outstanding selectivity and productivity. The enzyme is stabilized by divalent magnesium ions, 2-mercaptoethanol, and ammonium furmarate, and can be conveniently purified with high recovery.

5 Claims, 1 Drawing Figure

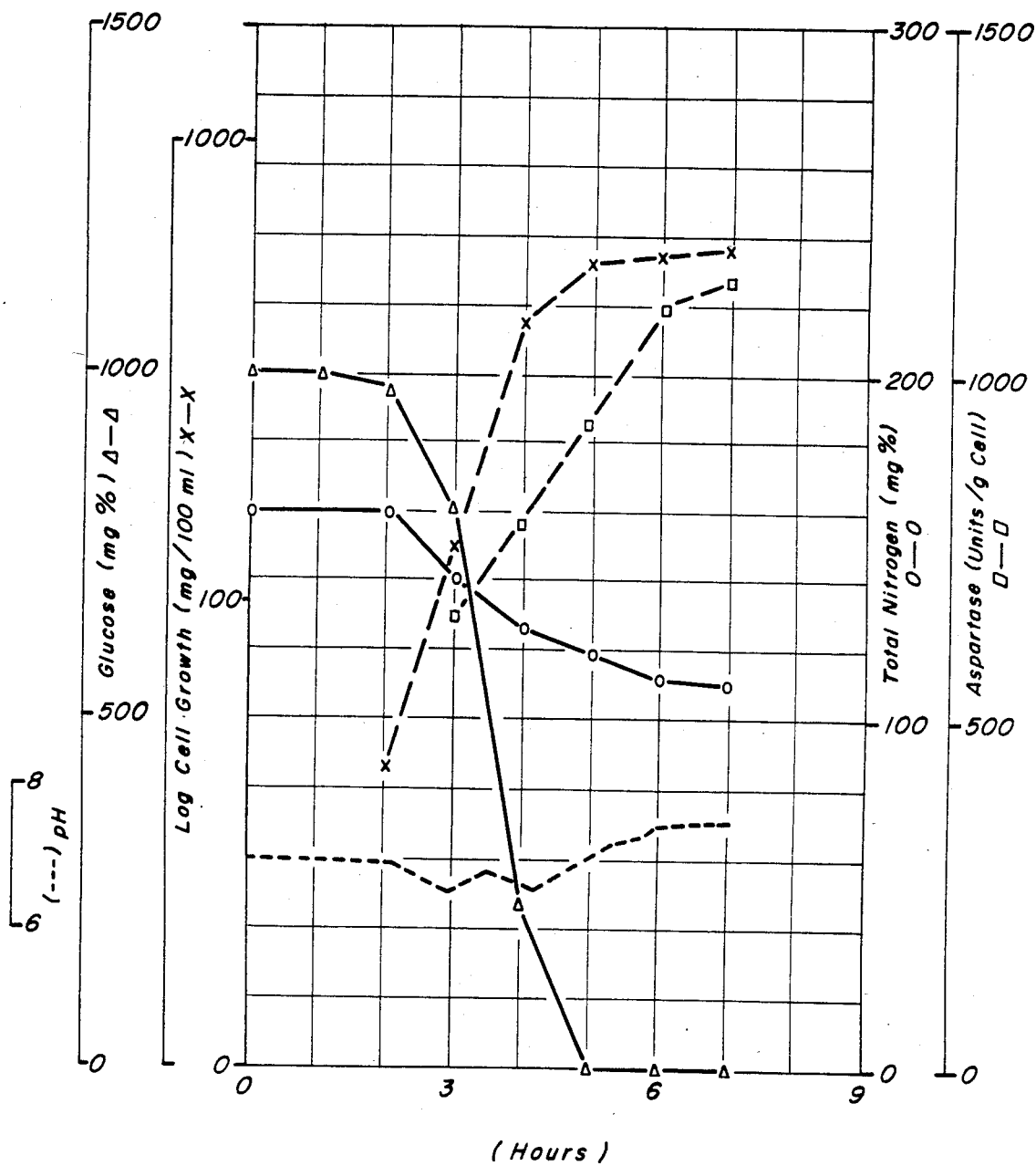
Growth Characteristics Of B. Subtilis Strain Asp-4

METHOD OF MAKING ASPARTIC ACID AND PURIFYING ASPARTASE

BACKGROUND OF THE INVENTION

Aspartic acid is one of the amino acids used by animals in the synthesis of proteins, and as such only L-aspartic acid is utilized. Although it is not an essential amino acid, which is to say that animals can synthesize this amino acid, it is nonetheless used as a feed additive, especially in Japan where production of synthetic L-aspartic acid in 1978 was 500–1,000 tons. Impacts of Applied Genetics: Micro-Organisms, Plants and Animals, Office of Technology Assessment. Aspartic acid also is used in seasoning industries. But whatever growth in L-aspartic acid production could be expected to result from the aforementioned uses is dwarfed by its anticipated growth as a component in the dipeptide sweetener, L-aspartyl-L-phenylalanine methyl ester. The demand of L-aspartic acid for this use alone is estimated at 1,000 metric tons per year by 1985 and double that by 1990.

A traditional chemical synthesis of L-aspartic acid has been frustrated by the necessity of resolving a racemic mixture, which is too costly to permit a commercially feasible process. Alternately, the obstacle to a total chemical synthesis of L-aspartic acid may be viewed as arising from the absence of a chiral catalyst which selectively synthesizes the L-enantiomer, or which would selectively destroy the D-enantiomer in a racemic mixture. However, nature has provided chiral catalysts in the form of enzymes, and enzymatic methods are the bases of L-aspartic acid production.

Aspartase is an enzyme which catalyzes the conversion of fumaric acid and ammonia to L-aspartic acid, as well as the reverse reaction of deamination of L-aspartic acid, that is,

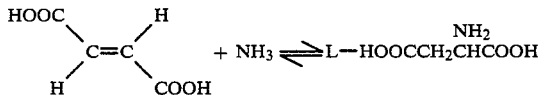

Aspartase itself can be produced by many micro-organisms, although not necessarily in quantities usable for a commercial process. Thus, U.S. Pat. No. 3,214,345 describes a method of producing L-aspartic acid by fermentation in a medium containing fumaric acid and ammonia using micro-organisms including *Pseudomonas fluorescens, Pseudomonas aeroginosa, Bacillus subtilis, Bacillus megatherium, Proteus vulgaris, Escherichia coli* and *Aerobacter aerogenes*. The patentees state that an important and critical feature of their invention is that the fermentation medium be sugar-free. The reason for this limitation is that whereas sugars promote the growth of the micro-organisms they concurrently repress aspartase production. A non-fermentative process for aspartic acid synthesis is decribed in U.S. Pat. No. 3,791,926 where the patentee immobilized an aspartase-producing micro-organism in a matrix formed by polymerizing a water-soluble monomer in an aqueous suspension of microbial cells. In comparing the synthetic methods based on immobilized cells with those based on immobilized aspartase the patentees found that substantial loss of enzyme activity occurred in extraction of aspartase from cells and subsequent concentration of the enzyme from the crude extract. The patentees thus developed and preferred a method of synthesis based on immobilized whole cells to obviate serious disadvantages encountered using immobilized aspartase itself.

In conceptualizing a method for producing L-aspartic acid several criteria can be elaborated. One is that the enzyme should be produced in high yield by a micro-organism which grows quickly using inexpensive growth media under non-stringent biological conditions. Another criterion is that the process should be heterogeneous so as to maximize utilization of aspartase. Because immobilized whole cells impose transport limitations arising both from the matrix itself and from the transport of substrate and product across the cell membrane, a method based on an immobilized enzyme is preferable. However, the latter method has additional requirements including the facile rupture of cell walls to release aspartase, stability of aspartase outside of the cell, and relative ease of purification, or at least concentration, of aspartase without catastrophic loss of enzyme or enzyme activity.

As is discussed more fully herein, I have succeeded in obtaining a micro-organism which grows rapidly under ordinary biological conditions using relatively inexpensive nutrients and which expresses aspartase, in part constitutively, in relatively high yields. The aspartase thus produced can be readily isolated and purified with good recovery, and is immobilized with relatively high efficiency. The resulting immobilized aspartase gives excellent production of L-aspartic acid from fumaric acid and ammonia over its usable lifetime.

An important advantage of the enzyme-producing microorganism of this invention is that maximum enzyme production and microbial growth can be obtained within about 7–8 hours, compared to a period of about 3 days when using a suitable *Escherichia coli*. Another important advantage, both unexpected and surprising, is that the micro-organism of this invention is quite sugar tolerant, which is to say that aspartase formation is not repressed by sugars even at levels of about 1.0 percent, and in fact aspartase production is increased by sugars such as glucose at levels up to about 1.0 percent. The advantage which accrues from such sugar tolerance is that aspartase can be formed via microbial growth using a relatively cheap and widely available energy source, namely, sugars. Still another advantage is the aspartase produced by the micro-organism of this invention is at least partly constitutive. Thus, although it is desirable to grow the micro-organism in the presence of, for example, L-aspartic acid to maximize enzyme production, L-aspartic acid is not an indispensable requirement for cellular aspartase production.

SUMMARY OF THE INVENTION

The object of this invention is to provide a method of making L-aspartic acid efficiently. An embodiment comprises contacting fumaric acid with the aspartase from *Bacillus subtilis*, strain ASP-4, NRRL B-15536. In a more specific embodiment the aspartase is immobilized on a support matrix of a porous refractory inorganic oxide impregnated with a polyamine and cross-linked by an access of a dialdehyde so as to provide pendant functional groups. In another embodiment the aspartase is stabilized toward loss of enzyme activity by the addition of a source of ammonium ions and fumaric acid. In yet another embodiment a stabilized crude enzyme solution is purified by a sequence of heating, protamine treatment, and salting out stages. Still other embodiments will become apparent from the description within.

DESCRIPTION OF THE FIGURE

The FIGURE shows several aspects of the fermentation of *Bacillus subtilis*, strain ASP-4, NRRL B-15536, as a function of time. In particular, it shows the depletion of glucose and total nitrogen from the fermentation medium, the cell growth, the production of aspartase, and the fluctuation of pH during the course of fermentation.

DESCRIPTION OF THE INVENTION

In one aspect my invention is an improved method of making L-aspartic acid by contacting an aqueous solution containing fumaric acid and a source of ammonia with the aspartase from the micro-organism ASP-4, NRRL B-15536, with the variant where the aspartase is immobilized being especially favored. A narrower aspect of my invention encompasses stabilizing aspartase toward loss of enzyme activity by adding a source of ammonium ion and fumaric acid to the enzyme. Yet another narrower aspect is the purification of a stabilized aspartase preparation by thermal denaturation of aspartase-inactive protein followed by protamine-induced precipitation of nucleic acids and subsequent salting out of aspartase from the remaining material.

The micro-organism of this invention, *Bacillus subtilis*, strain ASP-4, NRRL B-15536, arose from spontaneous adaptation of a parent strain which manifested no detectable aspartase production. That is to say, several generations of micro-organisms derived from the parent were grown in a medium containing L-aspartic acid and colonies showing good growth were screened for aspartase production. The best producer was given the designation ASP-4 and deposited in the Northern Regional Research Laboratory as NRRL B-15536.

One feature of the mutant of my invention is its rapid cell growth. Thus, for example, in a medium of 2% yeast extract and 1% glucose containing 10 mM each of ammonium sulfate and aspartic acid and 8.3 mM magnesium sulfate at pH 7.2, the micro-organism of this invention showed maximum growth within about 7-8 hours. Since enzyme production coincides with cell growth, which is not the case for all enzyme production, maximum enzyme production also is attained within about 7-8 hours. This compares with *E. coli* where maximum growth and enzyme production is attained only after a period from about 16 hours up to about 3 days.

Cell growth and aspartase production occurs in a nutrient medium containing an assimilable source of carbon, nitrogen and mineral nutrients under aerobic conditions. The nitrogen source is not critical and includes materials such as yeast extract, tryptone, soytone and peptone. Yeast extract appears to optimize aspartase production.

An outstanding feature of the micro-organism of this invention is its tolerance to sugars. Whereas other aspartase-producing micro-organisms have enzyme production strongly repressed by sugars, the micro-organism of this invention not only shows a high tolerance to sugars, but also shows maximum enzyme production in a medium containing about 1.0 percent of a sugar. Among the monosaccharides which can be utilized, cited solely for illustrative purposes, are included glucose, mannose, arabinose, fructose, galactose, and sorbose. Using glucose as an example, the sugar may repress aspartase formation in *E. coli* at levels as low as about 0.1%. In contrast, glucose stimulates formation of aspartase from the micro-organism herein and is preferably present in the medium at a level from about 0.3 to about 1.5 wt. %, especially from about 0.5 to about 1.3 wt. %.

It also has been found that ammonium ion stimulates the production of enzyme. Such stimulation is found in either the presence or absence of aspartic acid, and levels of ammonium ion between about 5 and about 20 mM are advantageously practiced in this invention.

Although the aspartase is at least partly constitutive, that is, the micro-organism produces aspartase even in the absence of an inducer, aspartase production is effectively maximized with small levels of aspartic acid. The presence of from about 5 to about 50 mmoles of aspartic acid per liter of fermentation broth is advantageously used, with a range between about 5 and about 15 being preferred. The optimum amount of aspartic acid depends on other nutrients, for example, the presence of ammonium ion and its concentration, the concentration of sugar, and so forth.

The aspartase produced by ASP-4 can be readily freed by breaking the cell walls and releasing the enzyme into solution. For example, after fermentation is complete cells may be collected, as for example by centrifugation, and washed to remove most of the growth medium. The cells can be resuspended in an aqueous medium and the cell walls ruptured by suitable means. Such methods include sonication, enzyme digestion of the cell wall, and grinding, including homogenization. Cell debris may then be removed, as for example by centrifugation, to give a crude extract containing the aspartase. Aspartase so produced shows a maximum enzyme activity at about 40° C. and at a pH of about 8.5.

The thermal stability of the native aspartase of this invention is increased by the presence of various addends. For example, in the absence of both divalent magnesium ions and 2-mercaptoethanol virtually all aspartase activity is lost within 20 hours at 4° C., whereas little activity is lost when both are present in an amount as low as about $10^{-4}$ molar, but preferably about $10^{-3}$ molar up to as high as about $10^{-}$molar. Thermal stability also is increased by the addition of polyols, such as glycerol and sorbitol, and by ammonium ions and fumaric acid (generally as fumarate). Thus, at 55° C. the aspartase in an aqueous solution containing $10^{-3}$ molar each of divalent magnesium ions and 2-mercaptoethanol loses all activity within about 15 minutes. However, when the enzyme is in a 20% aqueous sorbitol solution $10^{-3}$ molar in $Mg^{2+}$ and 2-mercaptoethanol it still retains almost half its activity after 60 minutes at 55° C. Finally, an aqueous solution of aspartase containing $10^{-3}$ molar each of $Mg^{2+}$ and 2-mercaptoethanol and 0.75 molar in ammonium fumarate retains about 90% of its activity after 60 minutes at 55° C. Although stabilization by ammonium ions and fumaric acid (or fumarate) occurs at concentrations as low as about 0.05 molar of each component, concentrations from about 0.3 to about 1 molar are preferable, with concentrations above about 1.5 molar conferring no additional benefit.

Often it is advantageous to purify the aspartase of this invention prior to its use in converting fumaric to aspartic acid, especially when the aspartase is to be immobilized. A method of purification which takes advantage of the relative thermal stability of aspartase in the presence of ammonium fumarate, divalent magnesium, and mercaptoethanol utilizes heating such an aspartase solution at 55° C. to denature foreign proteins, adding protamine after removal of denatured material to precipitate nucleic acids followed by adding a relatively large amount of salt after removal of the nucleic acids to salt out aspartase, which may then be recovered and optionally separated from salts by dialysis.

In particular, a solution of crude aspartase is first thermally stabilized by the addition of a divalent magnesium ion source and 2-mercaptoethanol to give a concentration of at least $10^{-4}$ molar of each, preferably a concentration from about $5 \times 10^{-4}$ to about $3 \times 10^{-3}$ molar. The resulting preparation is heated at a temperature between about 45° and 70° C., most desirably from about 50° to about 60° C., for a time sufficient to effect precipitation of aspartase-inactive protein while not causing denaturation of aspartase-active material. At 55° C. about 10 minutes suffices. The resulting mixture is cooled and solid is removed by suitable means, as by centrifugation.

Where the recovered solution contains nucleic acids, which will be the case where the crude aspartase solution is the whole cell extract, the nucleic acids can be selectively removed by addition of reagents such as protamine and streptomycin, especially as their water-soluble salts such as sulfates, nitrates, acetates, halides, and the like, preferably at temperatures less than about 10° C. Such reagents, and protamine sulfate is particularly preferred, are added to afford a concentration from about 0.001 to about 1.0 weight-volume percent, more particularly from about 0.01 to about 0.1 weight-volume percent. After allowing participation of the solids to occur for a period ranging from about 20 to about 40 minutes the solids are removed by suitable means, as by centrifugation, to afford a solution essentially free of nucleic acids.

The soluble aspartase is now separated from other protein material by precipitation with a salt at a temperature between about 0° and 10° C., generally between about 0° and about 5° C. A salt is added to the cooled solution in an amount equal to about 55% to about 65% of its saturation point, i.e., the total amount of salt which can be dissolved in the solution. In a preferred embodiment the salt must have a solubility such that about 4 molar aqueous solutions can be prepared at 0° C., but is otherwise without limitation. Examples of such salts include ammonium sulfate, ammonium acid sulfate, sodium chloride, potassium acetate, potassium carbonate, and potassium chloride. In another preferred embodiment the salt is an alkali metal or alkaline earth metal sulfate, such as $Li_2SO_4$, $Na_2SO_4$, $K_2SO_4$, and $MgSO_4$. When precipitation is complete, generally a period from about 5-60 minutes, purified aspartase is collected as the solid, using centrifugation for example. Where desired, salts may be removed from the aspartase by dialysis in a suitable buffer at a pH between about 6 and 8, generally stabilized with mercaptoethanol, divalent magnesium ion, and a polyol.

The aspartase of this invention may be used to convert fumaric acid to aspartic acid both as a free and as an immobilized enzyme, with the latter being greatly preferred. A particularly desirable immobilized aspartase results from the support matrix described in U.S. Pat. No. 4,141,857, which is a porous refractory inorganic oxide impregnated with a polyamine crosslinked by an excess of glutaraldehyde so as to provide pendant functional groups.

Immobilized aspartase of this invention shows outstanding selectivity in aspartic acid formation with equally outstanding productivity resulting from a combination of high activity and long half-life. For example, conversion of 99% fumaric to aspartic acid is possible using a fixed bed of my immobilized aspartase operating at a liquid hourly space velocity of about 40; for comparison, the patentee of U.S. Pat. No. 3,791,926 operated at an LHSV of 0.125 for a similar conversion level. Whether immobilized or free, the aspartase of this invention is used at a pH between about 7.0 and about 9.0, optimally between about 8.0 and 8.8, and at a temperature between about 25° C. and 60° C., most desirably between about 30° C. and 45° C. The presence of both divalent magnesium and mercaptoethanol in the feedstock is beneficial at a level between about $10^{-4}$ and about $10^{-2}$ molar for each. A source of ammonia is, of course, necessary for aspartic acid formation and is most conveniently supplied in the feedstock as ammonium fumarate.

Continuous production of aspartic acid may be achieved using immobilized aspartic as a fixed bed, fluidized bed, and so forth. A feedstock of ammonium fumarate, preferably at a pH between about 8.0 and 8.8, containing at least $10^{-4}$ molar each of divalent magnesium ions and mercaptoethanol, preferably from about $10^{-3}$ to $10^{-2}$ molar, heated to column operating temperature from about 30° C. to about 45° C. is passed through the bed at a rate so as to achieve the desired conversion of fumaric acid. With the immobilized aspartase of my invention a 99% conversion level is feasible. As the activity of the immobilized aspartase changes the liquid hourly space velocity of the feedstock is adjusted accordingly so as to maintain conversion, with the bed being usable and useful through its tenth life, i.e., that time when its activity is one-tenth its initial activity.

The following examples merely illustrate my invention, which is not limited thereto.

EXAMPLE 1

*Bacillus Subtilis*, strain ASP 4.

The parent micro-organism, *Bacillus subtilis* 1A1, was obtained from the *Bacillus subtilis* collection center at Ohio State University. This strain showed no detectable aspartase activity. All strains were stored on trypticase agar slants. For selection, the bacteria were grown on a medium containing ammonium sulfate (10 millimolar), magnesium sulfate (2 millimolar), aspartic acid (0.5%), potassium phosphate buffer (10 millimolar) at pH 7.0, and trace amounts of calcium chloride, manganese sulfate, and ferrous sulfate. The micro-organisms were transferred from agar slants to 50 ml. of medium and incubated for a time between about 20 and 24 hours at 32° C. with shaking. After several transfers in the same medium, the organisms were plated onto this medium containing 2% agar, and screening plates were incubated at 30°-32° C. for 2 days. Shake cultivations for testing aspartase activity were carried out in 250 ml. conical flasks containing 50 ml. of the above medium supplemented with 1% yeast extract. After cultivation for 16 hours, the bateria were removed by centrifugation at 12,000 rpm for 10 minutes. The cell mixture was resuspended, sonicated to rupture the cell walls, cell debris was removed by centrifugation and the supernatant was analyzed for aspartase activity.

Aspartase activity was assayed using aspartic acid as the substrate. The reaction mixture contained $5 \times 10^{-3}$ molar aspartic acid, $1 \times 10^{-2}$ molar tricine buffer, $2 \times 10^{-4}$ molar magnesium sulfate, $1 \times 10^{-3}$ molar mercaptoethanol at pH 8.5 1 ml. of the reaction mixture was placed in the spectrophotometric cell and preincubated in the spectrophotometer for at least 5 minutes at 40° C. A measured amount of supernatant, being the crude enzyme extract, was added to the reaction mixture and the reaction was allowed to proceed for 3 minutes at 40° C. Optical adsorption was measured every 60 seconds at 240 nm. One unit of aspartase activity is defined as 1 micromole of fumaric acid formed per minute. Protein was estimated by the biuret reaction with bovine serum albumin as the standard. The strain ASP-4 was selected for its high aspartase activity by this method.

ASP-4 was grown on a medium containing 2% yeast extract, 1% glucose, 10 mM ammonium sulfate, 10 mM aspartic acid, and 8.3 mM magnesium sulfate (1 g/l) at a pH of 7.0 at 37° C. Some growth characteristics in a 16 liter fermenter are reproduced in the FIGURE Growth rates were determined by measuring the dry weight of bacteria using an analytical microwave oven after washing the cells twice with water. Glucose in the medium was determined using a Beckmann glucose analyzer. Among the features demonstrated by the FIGURE are maximum growth within about 7-8 hours, enzyme production which coincides with cell growth, and utilization of glucose without repression of aspartase formation. Whereas maximum growth rate is exhibited at 37° C., one-half the maximum occurs at 25° C.

EXAMPLE 2

Aspartase dependence on pH, temperature.

The activity of the free aspartase was measured as a function of temperature and pH. These results are summarized in Table 1. In both tests a crude enzyme preparation was obtained as follows. Cells were suspended in a 0.05 M phosphate buffer, pH 7.0, containing $1 \times 10^{-3}$ M $MgSO_4$ and $1 \times 10^{-3}$ M mercaptoethanol and ruptured by sonication. Debris was removed by centrifugation at 13,000 rpm for 30 minutes, and the clear liquid used directly as the crude extract.

TABLE 1

Effect of Temperature (°C.) and pH on Aspartase Activity

| Activity (units/mL at 40° C.) | 0.65 | 1.90 | 2.55 | 2.85 | 3.35 | 1.60 | 1.30 | |
|---|---|---|---|---|---|---|---|---|
| pH | 7.0 | 7.75 | 8.0 | 8.25 | 8.5 | 8.75 | 9.0 | |
| Activity (units/mL, pH 8.5) | 1.70 | 3.60 | 3.90 | 4.20 | 4.50 | 4.20 | 3.60 | 2.60 |
| T, °C. | 23 | 31 | 35 | 38 | 41 | 44 | 48 | 51 |

EXAMPLE 3

Purification of aspartase.

250 grams of cell cake from 16 liters of fermentation broth was suspended in ammonium fumarate (0.75 M) at pH 8.5 and containing $1 \times 10^{-3}$ M each of magnesium sulfate and 2-mercaptoethanol. Crystalline egg white lysozyme, 30 mg, was added and the suspension was stirred for 16 hours at room temperature, after which it was sonicated. Cell debris was removed by centrifugation at 16,000 g for 30 minutes.

The supernatant was then heated at 55° C. for 10 minutes and the denatured protein which formed was removed by centrifugation. To the supernatant was added 100 ml of a 2.5 weight-volume percent solution of protamine sulfate. The mixture was stirred for 30 minutes at 4° C., after which precipitate was removed by centrifugation. Solid ammonium sulfate then was added to supernatant to a final concentration of 60% of saturation. After being stirred for 30 minutes at 4° C., the suspension was centrifuged at 16,000 g for 20 minutes and the aspartase-active solid was collected.

The precipitate was dissolved in 0.05 M potassium phosphate, pH 7.0, containing $1 \times 10^{-3}$ M each of magnesium sulfate and 2-mercaptoethanol and 20 percent glycerol. This enzyme solution was dialyzed against 4 liters of the same buffer for 16 hours. The course of aspartase purification is summarized in the following table.

TABLE 2

Purification of Aspartase

| Sample | Total Activity (units) | Activity, units/ml | Specific Activity (units/mg protein) |
|---|---|---|---|
| Crude extract | 70,190 | 65.6 | 2.18 |
| Heated extract | 72,270 | 73.0 | 2.91 |
| Solid from ammonium sulfate treatment | 61,380 | 372.0 | 11.6 |

As can be seen from the increase in specific activity, a 5.3-fold purification is achieved with an 87% recovery of aspartase.

EXAMPLE 4

Preparation of Immobilized Aspartase.

To a desired amount of polyethyleneimine impregnated alumina of 60/80 mesh was added 7.0 ml of a 1.5% aqueous solution of glutaraldehyde per gram of alumina at room temperature. The mixture was stirred for 30 minutes under vacuum, after which glutaraldehyde was thoroughly washed out with distilled water. A 0.1 molar solution of potassium phosphate at pH 7.0 is added to the glutaraldehyde crosslinked support, the mixture was stirred well and the liquid was decanted. This procedure was repeated until the pH of the supernatant is 7.0, at which time the excess buffer was removed by thorough washing with distilled water. Purified aspartase was offered to the support at a level of 2,000 units per gram of support contained in 10 ml of enzyme solution. The enzyme solution and support matrix were mixed at 4°C. overnight with intermittent shaking. Liquid was removed by decantation; adhering but unbonded enzyme was removed by copious washing of the immobilized enzyme system with water.

EXAMPLE 5

Half-Life of Immobilized Aspartase.

The thermal stability of immobilized aspartase was determined at 35°, 40°, and 45° C. using 3 grams of immobilized aspartase, prepared as described above, in a water-jacketed column used as a differential reactor. The feed for the reactors contained 1.5 M ammonium fumarate, $10^{-3}$ M each of magnesium sulfate and mercaptoethanol, pH 8.5 adjusted with ammonium hydroxide. The feedstock was pumped upflow through the reactors which were maintained at low conversion. Samples from the column were collected and aspartic acid concentration was determined by high pressure liquid chromatography. At 35° C., the half-life was about 90 days. At 40° C., the half-life was about 65 days; at 45° C., the half-life was about 30 days.

EXAMPLE 6

Stoichiometry and Selectivity of Immobilized Aspartase.

The stoichiometry of our immobilized aspartase, prepared as described in the previous examples, was determined using a 1 g column of immobilized aspartase, approximately 5,000 units per gram activity, operating at 40° C. The feedstock was 1.5 molar ammonium fumarate at pH 8.5 containing $10^{-3}$ molar each of magnesium sulfate and mercaptoethanol. The contents of the flask was circulated upflow through the jacketed column with the effluent being returned to the feed flask. The amount of fumaric acid consumed and aspartic acid formed was measured at various times using high-pressure liquid chromatography with results being summarized in Table 3.

TABLE 3

Stoichiometry of Immobilized Aspartase

| Circulation time hours | Aspartic acid formed (moles) | Fumaric acid consumed (moles) |
| --- | --- | --- |
| 0.5 | 0.383 | 0.380 |
| 2.0 | 0.962 | 0.929 |
| 3.0 | 1.195 | 1.193 |
| 4.0 | 1.346 | 1.347 |
| 5.0 | 1.398 | 1.411 |
| 22.0 | 1.447 | 1.479 |

As the above table clearly shows, the amount of aspartic acid formed is the same, within experimental error, as the amount of fumaric acid consumed.

350 ml of the above feedstock was passed through a column of immobilized aspartase to achieve at least 99% conversion of fumaric acid. The column effluent was adjusted to pH 2.8 with hydrochloric acid and cooled to 0° C. for 30 minutes, after which the solid which formed was collected by filtration. The solid was washed well with cold ethanol, sucked dry on a Buchner filter and collected to afford 67.6 g of aspartic acid, or 96.9% of the theoretical yield of 69.8 g.

The purity of the product so obtained was measured in various ways. Analysis by high pressure chromatography showed the sample contained 96.2% aspartic acid, 0.4% fumaric acid, with the remainder probably being ammonium chloride. After 2 recrystallizations from water adjusted to pH 2.8 with hydrochloric acid, the aspartic acid showed a specific rotation, $D^{21.0}$, of 25.5±1.2° (6N hydrochloric acid).

A sample was assayed by L-amino acid oxidase by measuring oxygen consumption manometrically according to the procedure described by W. W. Umbreit, R. H. Burris, and J. F. Stauffer, "Manometric Techniques," P. 203, Burgess Publishing Co., Minneapolis, Minn., 1964. The assay showed 97.1% purity of the L-aspartic acid formed.

EXAMPLE 7

Productivity of Immobilized Aspartase.

A feedstock of 1.5 M ammonium fumarate at pH 8.5 containing $10^{-3}$ M each of magnesium sulfate and 2-mercaptoethanol was passed through a column of immobilized aspartase, initial activity 5,000 units per gram, maintained at 40° C. at a liquid hourly space velocity sufficient to insure 99% conversion of fumaric acid. The initial LHSV was 40 with an initial productivity of 566.8 Kg aspartic acid per day per Kg immobilized aspartase. The column showed a half-life of about 50 days, with productivity at tenth-life of 38,000 Kg aspartic acid per kilogram immobilized aspartase.

In a similar experiment the initial LHSV to achieve 99% conversion was 38.2, initial productivity was 538.4 Kg aspartic acid per day per kilogram immobilized aspartase, and the productivity at tenth-life was 36,290 Kg aspartic acid per Kg immobilized aspartase.

What is claimed is:

1. A method of making L-aspartic acid comprising contacting an aqueous solution of fumaric acid containing a source of ammonia, 2-mercaptoethanol, and a source of divalent magnesium ions, each of the latter two at a concentration from about $10^{-4}$ to about $10^{-2}$ molar, at a temperature from about 25° C. to about 60° C. and a pH about 7.0 to about 9.0 with the aspartase from NRRL B-15536, and recovering the L-aspartic acid formed thereby.

2. A method of purifying aspartase comprising: (a) heating a thermally stabilized solution of aspartase to a temperature between about 45° C. and 70° C., removing the solids formed thereby and recovering the aspartase solution; (b) adding to the cooled solution a nucleic acid precipitating reagent selected from the group consisting of protamine, streptomycin, and their water-soluble salts in an amount to afford a concentration of said reagent from about 0.001 to about 1.0 weight-volume percent, removing the nucleic acids precipitated thereby and collecting the essentially nucleic acid-free enzyme solution; (c) adding to the latter solution at a temperature between about 0° C. and 10° C. salt in an amount equal to about 55% to about 65% of its saturation point; and (d) collecting the aspartase precipitated thereby.

3. The method of claim 2 where heating is from about 50° to about 60° C.

4. The method of claim 2 where the nucleic acid precipitating reagent is added in an amount between about 0.01 and 0.1%.

5. The method of claim 2 where the salt of step (c) has a minimum solubility of about 0° C. in water equivalent to that of about a 4 molar solution.

* * * * *